United States Patent [19]

Berstermann

[11] Patent Number: 4,556,315
[45] Date of Patent: Dec. 3, 1985

[54] PROCESS AND APPARATUS FOR THE EMISSION-SPECTROSCOPICAL TESTING OF METALLIC SAMPLES

[75] Inventor: Wilhelm Berstermann, Georgsmarienhütte, Fed. Rep. of Germany

[73] Assignee: Klöckner-Werke Aktiengesellschaft, Duisburg, Fed. Rep. of Germany

[21] Appl. No.: 446,051

[22] Filed: Dec. 1, 1982

[30] Foreign Application Priority Data

Dec. 2, 1981 [DE] Fed. Rep. of Germany ....... 3147642

[51] Int. Cl.$^4$ ............................................ G01N 21/67
[52] U.S. Cl. .................................................. 356/313
[58] Field of Search ............ 356/313; 315/207, 209 R, 315/209 CD, 240, 241 R, 242–244

[56] References Cited

U.S. PATENT DOCUMENTS 3,973,167 8/1976 Walters et al. ................. 315/243 X
4,296,358 10/1981 Bernier ......................... 315/209 CD

FOREIGN PATENT DOCUMENTS 12350 1/1982 Japan ................................... 356/313

Primary Examiner—F. L. Evans
Attorney, Agent, or Firm—Watson Cole Grindle & Watson

[57] ABSTRACT

During the emission-spectroscopical testing of metallic samples by means of unipolar discharges, material is precipitated onto the counterelectrode material which leads to faulty test results. According to the invention, at the start of the pre-spark period half waves of the unipolar discharge are replaced by oscillating discharges, wherein two parallel-connected discharge capacitors and two series-connected discharge resistors, one discharge capacitor and one discharge resistor can be shunted and the shunting is canceled out after a pre-specified period of time, starting with the pre-spark period.

3 Claims, 2 Drawing Figures

PROCESS AND APPARATUS FOR THE EMISSION-SPECTROSCOPICAL TESTING OF METALLIC SAMPLES

BACKGROUND OF THE INVENTION

This invention relates to the emission-spectroscopical testing of metallic samples in which a spark spectrum is produced between a metallic sample and a counter-electrode and is imaged onto a grating, in which the evaluation of the intensities of the spectral lines follows the production of an inert gas atmosphere and the pre-spark period.

The invention is concerned with stationary apparatuses which can also be designated as "quantometers" for the emission-spectroscopical or spectro-analytical testing of metallic samples. These tests are generally carried out in such a manner that initially the metallic samples are abraded on the surface so that a metallic surface is exposed. After placing the metallic sample in the stationary analytical apparatus, an inert gas atmosphere is produced, a discharge is then induced between the exposed surface of the metallic sample and a counterelectrode during the so-called pre-spark period, so that a substantially steady condition is established on the surface of the sample during the spark discharge. The pre-spark period is followed by the integration period, during which the amounts of charge, which are proportional to the intensities of the spectral lines, are integrated and subsequently evaluated. The spark spectra are produced, among other methods, by means of unipolar discharges, to which this invention refers in the following sections.

During a discharge, material vaporizes on the surface of the sample materials and is precipitated in part onto the counterelectrode. Since this can lead to faulty test results, the counterelectrode must be cleaned mechanically from time to time. This mechanical cleaning, however, is too cumbersome if the entire spectro-analytical testing is to occur fully automatically and within a short period of time.

SUMMARY OF THE INVENTION

Therefore, the object of the invention is to provide a process which makes it possible to automatically remove the precipitated material from the counterelectrode.

In accordance with the invention, this problem is solved in that, starting with the pre-spark period, half waves of the unipolar discharge are replaced by oscillating discharges in order to remove from the counterelectrode precipitated material of previously tested sample materials. These measures result in the removal of this material precipitated onto the counter-electrode during a fraction of the pre-spark period. In certain respects, this counterelectrode assumes the role of a sample material during this period.

In one advantageous development of the invention, the capacitance of the discharge capacitor and the resistance of the discharge resistor are to be reduced for a short time in order to be able to produce oscillating discharges.

According to one principle of the invention, the apparatus is characterized by two parallel-connected discharge capacitors, one of which can be shunted, and two series-connected discharge resistors, one of which can also be shunted.

According to another advantageous development of the invention, the apparatus has a counter which, after summing a predetermined number of oscillations of the primary circuit, activates a relay which cancels out the shunting of one discharge capacitor and one discharge resistor.

BRIEF DESCRIPTION OF THE DRAWINGS

The invention will now be described with reference to a specific embodiment shown in the drawing, in which.

DETAILED DESCRIPTION OF THE INVENTION

Figure 1:
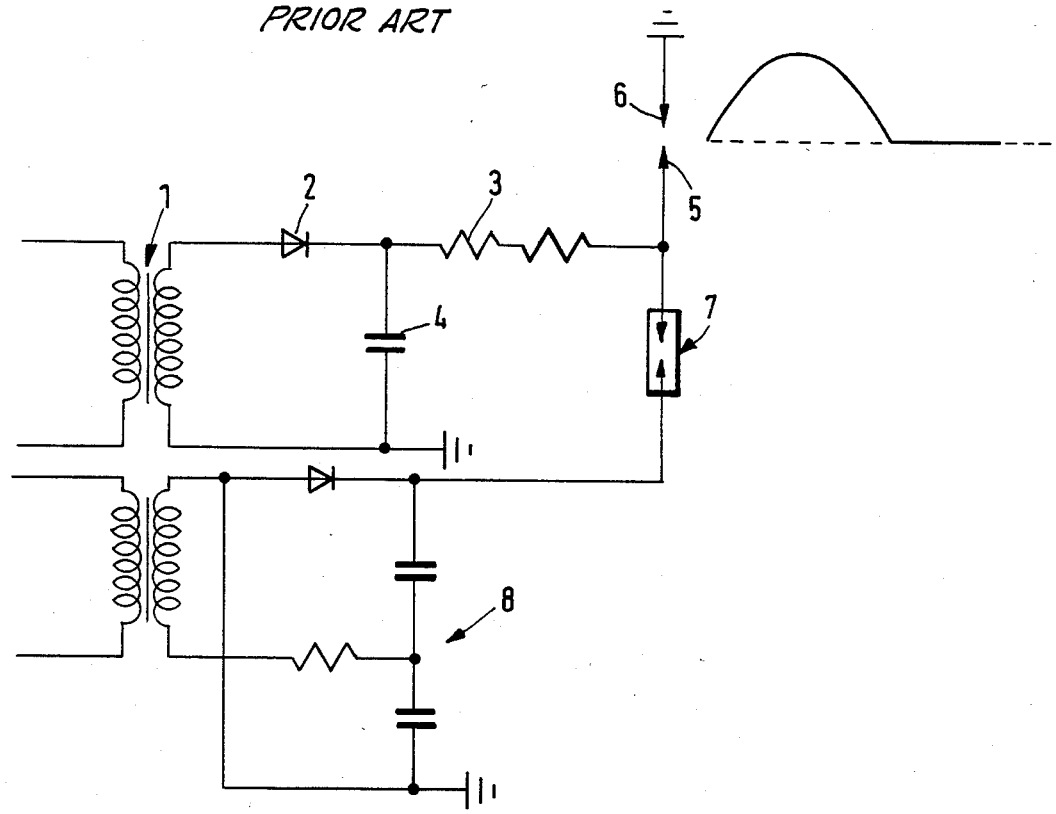
FIG. 1 shows a circuit for producing unipolar discharges in accordance with the state of the art.

In FIG. 1, a power transformer has in its secondary circuit a diode 2 connected in series with a discharge resistor 3. A grounded discharge capacitor 4 is provided parallel to the secondary winding of the transformer and to the diode. The counterelectrode 5 is connected downstream of the discharge resistor. Together with the grounded metallic sample 6 which is to be tested, it forms a spark gap for the production of unipolar discharges. A control spark gap 7 is connected upstream of the spark gap comprising sample and counterelectrode. This control spark gap 7 is operated by a known circuit 8 to double its voltage. The discharge produced between metallic sample and counterelectrode runs in half waves (unipolar discharges). During these half waves, material of the metallic samples to be tested is removed and a part thereof reaches the counterelectrode. The test readings are affected in the course of the measurement sequence. Heretofore, the counterelectrode was cleaned mechanically in order to overcome this drawback.

Figure 2:
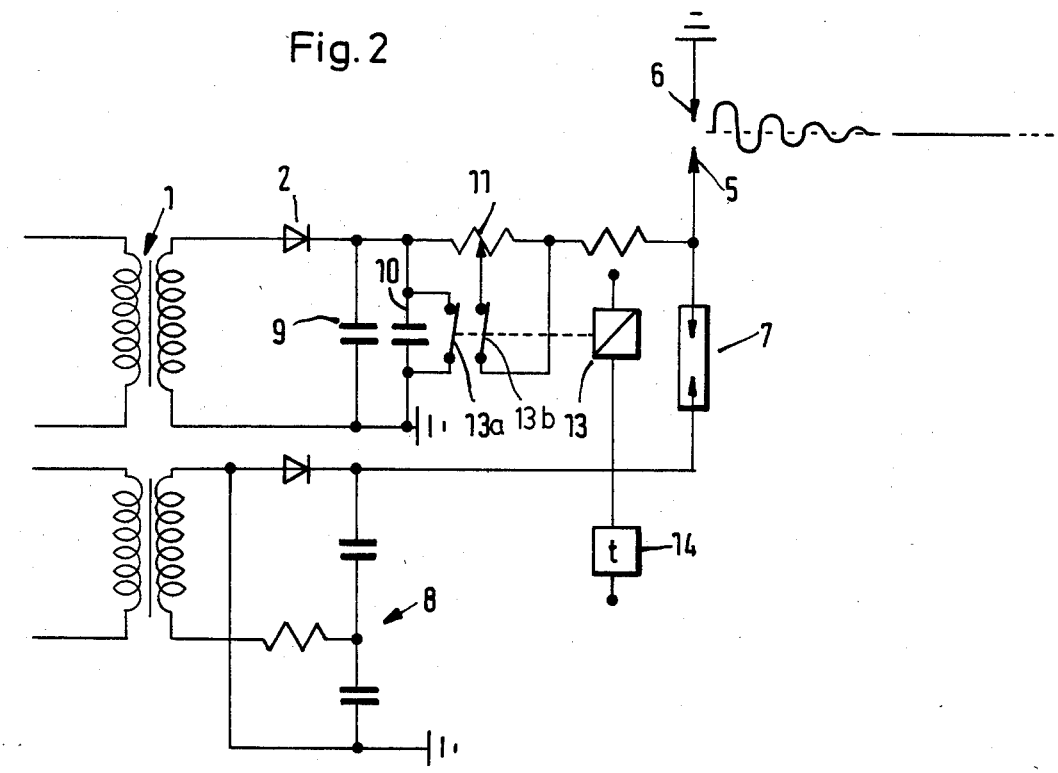
FIG. 2 shows the construction of this circuit in accordance with the invention.

In order to avoid this mechanical cleaning, especially in fully automatic installations, the counterelectrode is cleaned as follows: At the start of the pre-spark period the material deposition on the counterelectrode is removed in accordance with the invention by oscillating discharges. To accomplish this (see FIG. 2), the discharge capacitor 4 of FIG. 1 is replaced by parallel-connected discharge capacitors 9 and 10, while the discharge resistor 3 of FIG. 1 is replaced by a variable discharge resistor 11. The discharge capacitor 10 can be shunted and the resistance of variable discharge resistor 11 reduced to produce the aforementioned oscillating discharge. For this purpose, a relay 13 has been provided which is activated by a counter 14. At the start of the pre-spark period relay contacts 13a and 13b are closed and the counter counts a predetermined number of pulses which correspond to the oscillations in the primary circuit. As soon as the counter has counted a prespecified number of pulses, relay 13 is activated to open relay contacts 13a and 13b and cancel the shunting of the discharge capacitor 10 and reduction of the resistance of the discharge resistor 11, so that the oscillating discharges are converted into unipolar discharges.

I claim:

1. A power transformer for the emission-spectroscopical testing of a metallic sample by unipolar discharges of a spark spectrum during a spark period, comprising:

a primary circuit means and a secondary circuit means;

said secondary circuit means including a control spark gap and means for producing said spark spectrum by said unipolar discharges between the metallic sample and a counterelectrode;

said primary circuit controlling said secondary circuit;

said secondary circuit further including discharge capacitance means and discharge resistance means electrically connected to one another; and said primary circuit including means for changing at least one of the capacitance of said capacitance means and the resistance of said resistance means during a pre-spark period, whereby said secondary circuit means produces oscillating discharges during said pre-spark period to remove any material of the tested metallic sample precipitated onto said counterelectrode.

2. The power transformer as claimed in claim 1 wherein said discharge capacitance means includes two parallel-connected capacitors and said resistance means includes a variable resistance resistor, and said means for changing includes means for shunting one of said two parallel-connected capacitors and means for varying said variable resistance and being responsive to said primary circuit.

3. The power transformer as claimed in claim 2, wherein said means for changing further includes means for counting a preset number of said oscillating discharges, and a relay responsive to said means for counting, and a normally closed respective relay contact for shunting said one capacitor and for shunting a portion of said variable resistance at the initiation of counting, and the respective relay contacts being opened with said counting means counting to said preset number.

* * * * *